United States Patent [19]

Schmidt et al.

[11] Patent Number: 5,026,951
[45] Date of Patent: Jun. 25, 1991

[54] PROCESS FOR PARAFFIN ISOMERIZATION WITH LIQUID PHASE ADSORPTIVE PRODUCT SEPARATION

[75] Inventors: Robert J. Schmidt, Rolling Meadows; Lynn H. Rice, Palatine; Srikantiah Raghuram, Darien, all of Ill.

[73] Assignee: UOP, Des Plaines, Ill.

[21] Appl. No.: 462,262

[22] Filed: Jan. 9, 1990

[51] Int. Cl.[5] .............................................. C07C 5/13
[52] U.S. Cl. .................................. 585/738; 585/748; 585/751; 585/820; 585/826
[58] Field of Search ............... 585/738, 748, 751, 820, 585/826

[56] References Cited

U.S. PATENT DOCUMENTS

| 2,935,467 | 5/1960 | Fleck et al. | 585/826 |
|---|---|---|---|
| 2,938,864 | 5/1960 | Fleck et al. | 585/826 |
| 2,966,528 | 12/1960 | Haensel | 260/266 |
| 3,160,585 | 12/1964 | Mettox et al. | 585/820 |
| 3,184,406 | 5/1965 | Yeo et al. | 585/826 |
| 3,184,518 | 5/1965 | Sanders et al. | 585/826 |
| 3,201,491 | 8/1965 | Stime et al. | 585/826 |
| 3,755,144 | 8/1973 | Asselin | 208/95 |
| 4,717,784 | 1/1988 | Stem et al. | 585/738 |
| 4,804,802 | 2/1989 | Evans et al. | 585/734 |

Primary Examiner—Curtis R. Davis
Attorney, Agent, or Firm—Thomas K. McBride; John G. Tolomei

[57] ABSTRACT

A combination isomerization and liquid phase adsorptive separation process is given increased efficiency and cost effectiveness by the elimination of a column for the separation of desorbent material from selectively retained components. By decreasing the ratio of normal paraffin desorbent to the selective pore volume circulation rate, the extract column can be eliminated without providing other means for the rejection or recovery of desorbent material. This reduction in the ratio of normal paraffin desorbent to selective pore volume circulation rate has been found not to decrease the recovery from the adsorption section. The elimination of the column provides a substantial decrease in the cost of the equipment to operate a combination isomerization zone and liquid phase adsorption section. In an alternate arrangement, the extract column is replaced with a deisohexanizer column. The deisohexanizer column can be used to produce a $C_5$–$C_6$ product stream having research octane numbers of 93 or greater.

17 Claims, 3 Drawing Sheets

PROCESS FOR PARAFFIN ISOMERIZATION WITH LIQUID PHASE ADSORPTIVE PRODUCT SEPARATION

BACKGROUND OF THE INVENTION

This invention relates generally to the isomerization of hydrocarbons. This invention relates more specifically to the isomerization of light paraffins using a solid catalyst, and the separation of more highly branched paraffins from less highly branched paraffins by adsorptive separation.

DESCRIPTION OF THE PRIOR ART

High octane gasoline is required for modern gasoline engines. Formerly it was common to accomplish octane number improvement by the use of various lead-containing additives. As lead is phased out of gasoline for environmental reasons, it has become increasingly necessary to rearrange the structure of the hydrocarbons used in gasoline blending in order to achieve high octane ratings. Catalytic reforming and catalytic isomerization are two widely used processes for this upgrading.

A gasoline blending pool normally includes $C_4$ and heavier hydrocarbons having boiling points of less than 205° C. (395° F.) at atmospheric pressure. This range of hydrocarbon includes $C_4$–$C_6$ paraffins and especially the $C_5$ and $C_6$ normal paraffins which have relatively low octane numbers. The $C_4$–$C_6$ hydrocarbons have the greatest susceptibility to octane improvement by lead addition and were formerly upgraded in this manner. Octane improvement can also be obtained by using isomerization to rearrange the structure of the paraffinic hydrocarbons into branched-chain paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branched-chain isoparaffins. Although the $C_6$ and heavier hydrocarbons can be upgraded into aromatics through hydrocyclization, the conversion of $C_6$'s to aromatics creates higher density species and increases gas yields with both effects leading to a reduction in liquid volume yields. Therefore, it is common practice to charge the $C_6$ paraffins to an isomerization unit to obtain $C_6$ isoparaffin hydrocarbons. Consequently, octane upgrading commonly uses isomerization to convert $C_6$ and lighter boiling hydrocarbons and reforming to convert $C_7$ and higher boiling hydrocarbons.

The effluent from an isomerization reaction zone will contain a mixture of more highly branched and less highly branched paraffins. In order to further increase the octane of the products from the isomerization zone, normal paraffins, and sometimes less highly branched isoparaffins, are typically recycled to the isomerization zone along with the feed stream in order to increase the ratio of less highly branched paraffins to more highly branched paraffins entering the isomerization zone. A variety of methods are known to treat the effluent from the isomerization zone for the recovery of normal paraffins and monomethyl branched isoparaffins for recycling these less highly branched paraffins to the isomerization zone.

U.S. Pat. No. 2,966,528 issued to Haensel discloses a process for the isomerization of $C_6$ hydrocarbons and the adsorptive separation of normal hydrocarbons from branched chain hydrocarbons. The process adsorbs normal hydrocarbons from the effluent of the isomerization zone and recovers the unadsorbed hydrocarbons as product, desorbs straight chain hydrocarbons using a normal paraffin desorbent, and returns the desorbent and adsorbed straight chain hydrocarbons to the isomerization zone.

U.S. Pat. No. 3,755,144 shows a process for the isomerization of a pentane/hexane feed and the separation of normal paraffins from the isomerization zone effluent. The isomerization zone effluent is separated by a molecular sieve separation zone that includes facilities for the recovery of desorbent from the normal paraffin containing stream that is recycled to the isomerization zone. An extract stream that contains isoparaffins is sent to a deisohexanizer column that separates isopentane and dimethyl butane as a product stream and provides a recycle stream of isohexane that is returned to the isomerization zone.

U.S. Pat. Nos. 4,717,784 and 4,804,802 disclose processes for the isomerization of a hydrocarbon feed and the use of adsorptive separation to generate normal paraffin and monomethyl-branched paraffin recycle streams. The effluent from the isomerization zone enters a molecular sieve separation zone that contains a 5A-type sieve and a ferrierite-type sieve that adsorb normal paraffins and monomethyl-branched paraffins, respectively. U.S. Pat. No. 4,804,802 discloses steam or hydrogen as the desorbent for desorbing the normal paraffins and monomethyl-branched paraffins from the adsorption section and teaches that steam or hydrogen may be recycled with the normal paraffins or monomethyl-branched paraffins to the isomerization zone.

One method of separating normal paraffins from isoparaffins uses adsorptive separation under liquid phase conditions. In such methods, the isomerization effluent contacts a solid adsorbent having a selectivity for normal paraffins to effect the selective adsorption of normal paraffins and allow recovery of the isoparaffins as a high octane product. Contacting the normal paraffin containing adsorbent with the desorbent material in a desorption step removes normal paraffins from the adsorbent for recycle to the isomerization zone. Both the isoparaffin and normal paraffin containing streams undergo a separation for the recovery of desorbent before the isoparaffins are recovered as a product and the normal paraffins recycled to the isomerization zone. Liquid phase adsorption has been carried out in conventional swing bed systems as shown in U.S. Pat. No. 2,966,528. The use of simulated moving bed systems for the selective adsorption of normal paraffins is also known and disclosed by U.S. Pat. No. 3,755,144. Simulated moving bed systems have the advantage of increasing recovery and purity of the adsorbed and non-adsorbed components in the isomerization zone effluent for a given unit of adsorbent material.

In liquid phase adsorption systems the adsorbent contains selective pores that will more strongly adsorb the selectively adsorbed components in the feed mixture. The selective pore volume is limited and the quantity of such pores must accommodate the desired volume of components to be adsorbed from the feed mixture. The desorbent material is also a selectively adsorbed component. Therefore, the extract column is used to recover desorbent, otherwise any desorbent that passes through the reactors of the isomerization zone and enters the adsorption section increases the amount of adsorbed component in the feed mixture and requires additional adsorbent. If the quantity of selectively adsorbed components is increased without increasing the available selective pore volume for a given unit of feed, it was believed that the purity of the extract and raffinate streams from the adsorption section decreases. Therefore, eliminating the extract column also affects the desorption stage of the adsorption section since the loaded adsorbent contains normal paraffins and desorbent material as adsorbed components; all of these desorbed components must be displaced by the desorbent. Without the extract column, increasing the desorbent flow during the desorption step and while maintaining the traditional desorbent to pore volume ratio will place a greater quantity of desorbent in circulation and increase the amount of selective pore volume needed during the feed step of the adsorption process. Under the conventional system, without some method of rejecting desorbent material from the recycled extract stream, the selective pore volume and desorbent requirements would continue to progressively increase.

Accordingly, it is an object of this invention to make processes for the isomerization and its liquid phase adsorptive separation of isomerization effluents more economical.

Another object of this invention is to reduce the necessary equipment for the liquid phase adsorptive separation of normal and isoparaffins.

Another object of this invention is to provide a more cost effective arrangement for an isomerization of normal paraffins and the recycle of normal paraffins using liquid phase adsorptive separations.

SUMMARY OF THE INVENTION

Applicants have discovered that the amount of desorbent needed for the desorption step is much lower than expected when the adsorbent is loaded with desorbent material as well as the selectively adsorbed components. The lower desorbent requirement reduces the amount of desorbent that is recycled through the isomerization zone and can limit, advantageously, the amount of desorbent that re-enters the separation zone with the adsorption section feed mixture. By discovering that the desorbent requirements for the desorption step are lower when the adsorbent is loaded with the desorbent material and selectively adsorbed components, the adsorption section can operate continuously with only a small increase in the required adsorbent material. Similarily, the isomerization zone requires only a small increase in size to accommodate the small amount of additional desorbent material that is in circulation.

The adsorption section of an isomerization-adsorption combination previously used two columns, one to recover desorbent from an extract stream that contains the adsorbed normal paraffins and desorbent, and the other to recover desorbent from a raffinate stream that contains the unadsorbed isoparaffins. This invention is the combination of an isomerization zone and a liquid phase adsorptive separation zone for the production of isoparaffins wherein the extract column for separation of desorbent from normal paraffins is eliminated. Surprisingly, it has been discovered that the isomerization and adsorptive separation sections can be operated without the extract column and without a major increase in either reactor size or adsorbent volume. The fact that the extract column can be eliminated with only a minor increase in the isomerization reactor size and the adsorption volume is indeed surprising in light of the conventional operation of a liquid phase adsorption section.

Accordingly, in a broad embodiment, this invention is a process for the isomerization of hydrocarbons that incorporates a liquid phase adsorptive separation section for the recycle of normal hydrocarbons and does not use an extract column for the separation of desorbent from a straight chain hydrocarbon containing stream that is recycled to the isomerization zone. The specific steps of the process include passing the feed stream comprising straight chain hydrocarbons to an isomerization zone and passing a recycle stream comprising straight chain hydrocarbons and desorbent to the isomerization zone. The recycled stream and feed stream are contacted with an isomerization catalyst in the isomerization zone and recovered as an isomerization zone effluent that comprises branched chain hydrocarbons, straight chain hydrocarbons and desorbent. The isomerization zone effluent passes through an adsorption section where it is contacted with a desorbent containing adsorbent, which is selective for straight chain hydrocarbons, to adsorb the straight chain hydrocarbons and produce a first stream comprising desorbent and branched chain hydrocarbons, and an adsorbent containing straight chain hydrocarbons. The desorbent material is separated from the first stream and a product stream rich in branched chain hydrocarbons is recovered. The straight chain hydrocarbons are desorbed from the adsorbent that was previously contacted with the feed stream and contains straight chain hydrocarbons by contacting the adsorbent with a quantity of desorbent that is reduced relative to the usual practice and thereby producing the recycle stream that contains straight chain hydrocarbons and desorbent, and the desorbent containing adsorbent.

In a more specific embodiment, this invention is a process for the isomerization of $C_5$–$C_6$ hydrocarbons. This process includes steps of passing a feed stream comprising $C_5$–$C_6$ normal paraffins to an isomerization zone and passing a recycle stream comprising $C_5$ and $C_6$ normal paraffins in admixture with a normal butane desorbent to the isomerization zone. The feed stream and recycle stream are contacted in the isomerization zone with an isomerization catalyst to produce an effluent comprising $C_5$ and $C_6$ isoparaffins, $C_5$ and $C_6$ normal paraffins and the butane desorbent. The isomerization zone effuent is passed to a stabilizer section that separates the effluent into an overhead stream containing any excess butane desorbent and any lighter material and a stabilized stream comprising $C_5$ and $C_6$ normal paraffins, $C_5$ and $C_6$ isoparaffins and normal butane in an amount equal to 10 to 20 wt. % of the $C_5$ and $C_6$ normal paraffins in the stabilized stream. The stabilized stream is passed through an adsorption section as a feed mixture and is therein contacted with an adsorbent selective for normal paraffins to separate the isoparaffins from the normal paraffins. The adsorption section operates by maintaining a net fluid flow through at least three operationally distinctive serially interconnected zones of adsorbent in the adsorption section. These zones include an adsorption zone which is defined by the adsorbent located between the feed input stream at an upstream boundary and a raffinate output stream at a downstream boundary of the zone, a purification zone immediately upstream from the adsorption zone, which is defined by the adsorbent located between an extract output stream at an upstream boundary and the feed input stream at the downstream boundary of the purification zone, and a desorption zone immediately upstream from the purification zone, which is defined by the adsorbent located between a desorbent input stream at an upstream boundary and the extract output stream at a downstream boundary of the zone. The feed mixture enters the adsorption zone at adsorption conditions that effect the selective adsorption of the normal paraffins by the adsorbent so that a raffinate output stream is removed from the adsorption zone. Normal butane is passed into the desorption zone at desorption conditions to displace the $C_5$ and $C_6$ normal paraffins from the adsorbent in the desorption zone. An extract output stream comprising $C_5$ and $C_6$ normal paraffins and a normal butane desorbent is withdrawn from the desorption zone and a raffinate output stream comprising $C_5$ and $C_6$ isoparaffins and normal butane desorbent is withdrawn from the adsorption zone. The feed input stream, the raffinate output stream, the desorbent input stream, and the extract output stream are periodically advanced through the columns to effect the shifting of zones through the adsorbent and the production of the extract output and raffinate output streams. The normal butane desorbent is separated from the raffinate output stream and at least a portion of the normal butane is returned to the adsorption zone as the desorbent input stream to recover a product stream rich in $C_5$ and $C_6$ isoparaffins. At least a portion of the extract output stream is returned to the isomerization zone as the recycle stream without intermediate separation for the recovery of desorbent.

In another aspect of this invention, the isoparaffin containing product stream enters an additional separation section to separate less highly branched isoparaffins from more highly branched isoparaffins. The less highly branched isoparaffins, in particularly monomethyl branched isoparaffins and more particularly methylpentane, are recycled to the isomerization section to further increase the octane of an isoparaffin product stream.

Other objects, embodiments, and aspects of this invention are described in the following detailed description of the invention.

DETAILED DESCRIPTION OF THE INVENTION

Figure 1:
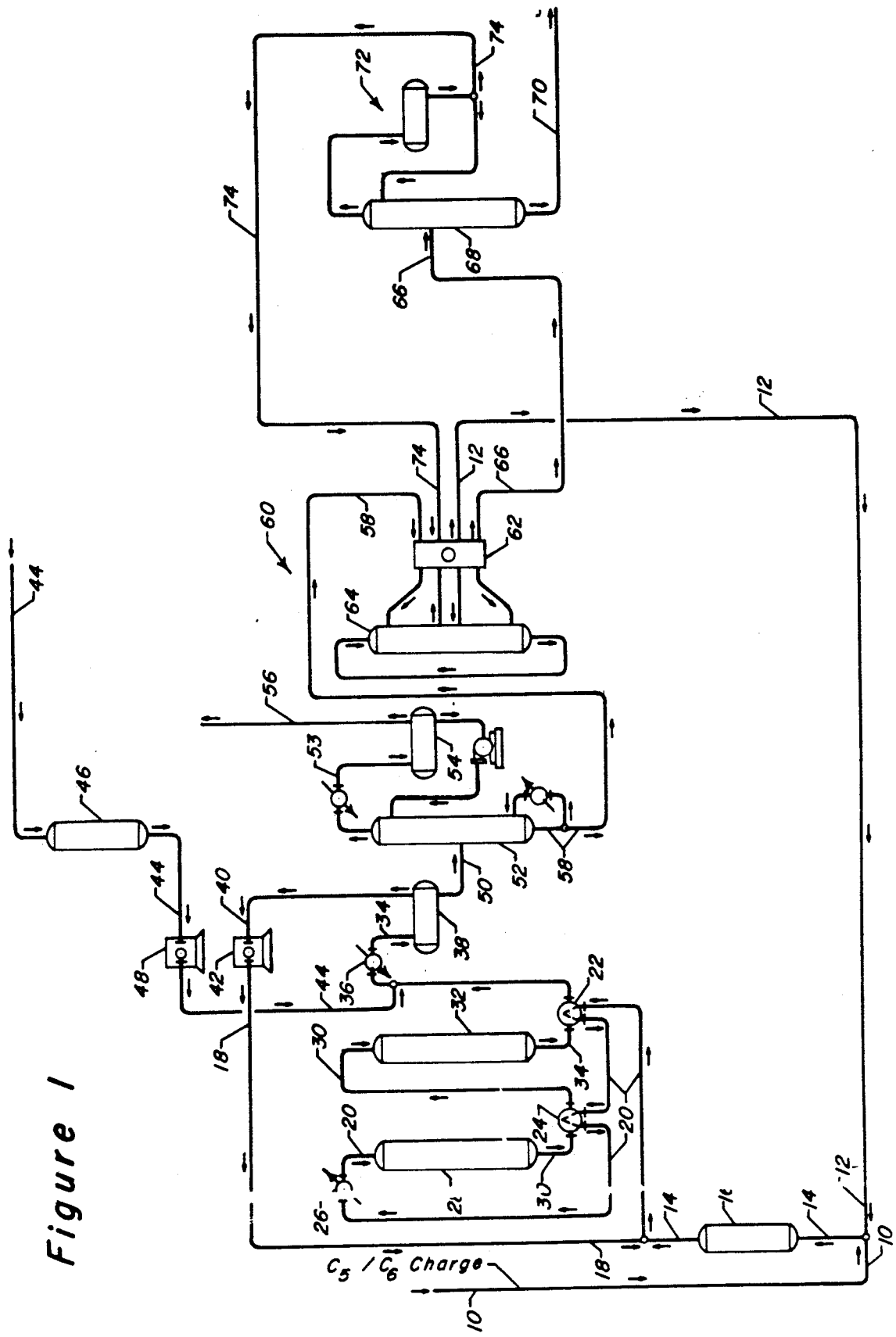
FIG. 1 is a schematic diagram with a flow arrangement for a combination isomerization and liquid phase adsorption process arranged in accordance with this invention.

This invention uses the combination of an isomerization zone and a liquid phase adsorptive separation section. The invention is not restricted to any particular type of isomerization zone or liquid phase adsorptive section. The isomerization zone can consist of any type of isomerization zone that takes a stream of straight chain hydrocarbons or a mixture of straight chain and branched chain hydrocarbons and partially converts straight chain hydrocarbons in the feed mixture to branched chain hydrocarbons thereby producing an effluent having branched chain and straight chain hydrocarbons. The liquid phase adsorption sections can utilize any type of a well known adsorption process such as a swing bed, simulated moving bed, or other schemes for contacting the adsorbent with the feed mixture and desorbing the feed mixture from the adsorbent with the desorbent material.

The process begins by charging a feed mixture to the isomerization zone. The feed mixture will contain straight chain hydrocarbons. The straight chain hydrocarbons are usually normal paraffins. In most combinations, the normal paraffins will have between 5 and 6 carbon atoms. The feed mixture may also contain a major or minor part of branched chain hydrocarbons especially isoparaffins with a corresponding number of carbon atoms to the normal paraffins. Light or heavy hydrocarbons may also be present in the feed mixture along with some light gases.

In accordance with this invention, a recycle stream of straight chain hydrocarbons will also enter the isomerization zone. This recycle stream may be mixed with the feed to form a combined charge.

This invention is described in the context of a process for the isomerization of $C_5$ and $C_6$ normal paraffins, the adsorption of normal paraffins in an adsorptive separation zone, and the desorption of normal paraffins using a butane desorbent. The description of this invention and the context of the specific embodiment related to $C_5$ and $C_6$ paraffin isomerization is not meant to limit this invention to the details disclosed herein.

The feedstocks that could be used in this invention include hydrocarbon fractions rich in $C_4$–$C_6$ normal paraffins. The term "rich" is defined as a stream having more than 50% of the mentioned component. Preferred feedstocks are substantially pure normal paraffin streams having from 4–6 carbon atoms or a mixture of such substantially pure normal paraffins. Other useful feedstocks include light natural gasoline, light straight run naphtha, gas oil condensates, light raffinates, light reformate, light hydrocarbons, fuel butanes, and straight-run distillates having distillation end points of about 77° C. (170° F.) and containing substantial quantities of $C_4$–$C_6$ paraffins. The feed may also contain low concentrations of unsaturated hydrocarbons and hydrocarbons having more than 6 carbon atoms. The concentration of these materials should be limited to 10 wt. % for unsaturated compounds and 20 wt.% for heavier hydrocarbons in order to restrict hydrogen consumption in cracking reactions. The feed in any normal paraffin recycle are combined and typically enter the isomerization zone with a hydrogen recycle stream.

Hydrogen is admixed with the feed in an amount that will provide a hydrogen to hydrocarbon molar ratio of from 0.01 to 10 in the effluent from the isomerization zone. Preferably, the hydrogen to hydrocarbon ratio is in the range of 0.05 to 5. Although no net hydrogen is consumed in the isomerization reaction, the isomerization zone will have a net consumption of hydrogen often referred to as the stoichiometric hydrogen requirement which is associated with a number of side reactions that occur. These side reactions include saturation of olefins and aromatics cracking and disproportionation. For feeds having a high level of unsaturates, satisfying the stoichiometric hydrogen will require a higher hydrogen to hydrocarbon ratio for the feed at the inlet of the isomerization zone. Hydrogen in excess of the stoichiometric amounts for the side reactions is often maintained in the reaction zone to provide stability and conversion by compensating for variation in feed stream compositions that alter the stoichiometric hydrogen requirements. Higher hydrogen to hydrocarbon ratios are often used to prolong catalyst life by suppressing side reactions such as cracking and disproportionation. When such side reactions occur, they can reduce conversion and lead to formation of carbonaceous compounds, usually referred to as coke, that foul the catalyst.

It has recently been found that the hydrogen to hydrocarbon ratio in isomerization zones that use a chlorided platinum alumina catalyst can be reduced significantly. In such cases, it is desirable to reduce the amount of hydrocarbon that enters the isomerization zone such that the hydrogen to hydrocarbon ratio of the effluent from the isomerization zone is less than 0.05. Reduced hydrogen to hydrocarbon ratios have been used based on the finding that the amount of hydrogen needed for suppressing coke formation need not exceed dissolved hydrogen levels. The amount of hydrogen in solution at the normal conditions of the isomerization zone effluent are preferably in a ratio of from 0.02 to 0.01. The amount of excess hydrogen over the stoichiometric requirement that is required for good stability and conversion is in a ratio of 0.01 to less than 0.05.

When the hydrogen to hydrocarbon ratio exceeds 0.05, it is not economically desirable to operate the isomerization zone without the recycle of hydrogen to the isomerization zone. Therefore, in such cases, recovery facilities for hydrogen from the effluent will be provided as herinafter described. Hydrogen may be added to the feed mixture in any manner that provides the necessary control for the addition of the hydrogen.

The hydrogen and hydrocarbon feed mixture is contacted in the reaction zone with an isomerization catalyst. The catalyst composites that can be used in the isomerization zone include traditional isomerization catalysts. Such catalysts include high chloride catalyst on an alumina base containing platinum, and crystalline aluminosilicates or crystalline zeolites. Suitable catalyst compositions of this type will exhibit selective and substantial isomerization activity under the operating conditions of the process.

As a class, the crystalline aluminosilicate or crystalline zeolite catalysts comprise crystalline zeolitic molecular sieves having an apparent pore diameter large enough to adsorb neopentane. A silica alumina molar ratio $SiO_2:Al_2O_3$ of greater than 3; less than 60 and preferably between 15 and 30 is desirable. In preferred form, the zeolite will contain an equivalent percent alkali metal cations and will have those $AlO_4$-tetrahedra not associated with alkali metal cations; either not associated with any metal cations or associated with divalent or other polyvalent metal cations. Usually the molecular sieve is a mordenite molecular sieve which is essentially in the acid form or is converted to the acid form. Particularly preferred catalysts of this type for isomerization are disclosed in detail in U.S. Pat. Nos. 3,442,794 and 3,836,597.

The preferred isomerization catalyst for this invention is a chlorided platinum alumina catalyst. The aluminum is preferably an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process. The chloride component termed in the art "a combined chloride" is present in an amount from about 2 to about 10 wt. % based upon the dry support material. The use of chloride in amounts greater than 5 wt. % have been found to be the most beneficial for this process. The inorganic oxide preferably comprises alumina and more preferably gamma-alumina, eta-alumina, and mixtures thereof.

There are a variety of ways for preparing the catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-aluminum catalyst base. An alternate method of increasing the chloride concentration in the final catalyst composite is to use an aluminum hydrosol to form the aluminum carrier material such that the carrier material also contains at least a portion of the chloride. Halogen may also be added to the carrier material by contacting the calcined carrier material with an aqueous solution of the halogen acid such as hydrogen chloride.

It is generally known that high chlorided platinum-alumina catalysts of this type are highly sensitive to sulfur and oxygen-containing compounds. Therefore, the use of such catalysts requires that the feedstock be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$-$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feed stream by hydrotreating. A variety of commercial dryers are available to remove water from the feed components. Adsorption processes for the removal of sulfur and water from hydrocarbon streams are also well known to those skilled in the art.

A preferred composition of zeolitic catalyst for use in the present invention comprises a Group VIII noble metal, a hydrogen form crystalline aluminosilicate, and a refractory inorganic oxide with the catalyst composition having a surface area of at least 580 m$^2$/g. Significant improvements in isomerization performance are realized when the surface area of the catalytic composite is at or above 580 m$^2$/g. A Group VIII metal is incorporated into the catalytic composite to supply a hydrogenation/dehydrogenation function and the preferred Group VIII noble metal is platinum. The Group VIII noble metal is present in an amount from about 0.01 to 5% by weight of the composite and preferably in an amount of at least 0.15% by weight but not over 0.35% by weight. The zeolitic catalytic composite may also contain a catalytically effective amount of promoter metal such as tin, lead, germanium, cobalt, nickel, iron, tungsten, chromium, molybdenum, bismuth, indium, gallium, cadmium, zinc, uranium, copper, silver, gold, tantalum, or one or more of rare earth metals and mixtures thereof. The hydrogen-formed silica alumina has either a three-dimensional or channel pore structure crystal lattice framework. The three-dimensional aluminosilicates include both synthetic and naturally occurring silica aluminas such as faujasites, which include X-type, Y-type, ultrastable-Y, and the like. L-type, omega-type, and mordenite are examples of the channel pore structure crystalline aluminosilicates. Mordenite, in either naturally occurring or synthetic form are preferred, particularly with a silica to alumina ratio of at least 16:1. The hydrogen form aluminosilicate may be present in an amount within the range of 50 to about 99.5 wt. %, preferably within the range of 75 to about 95 wt. %, and a refractory inorganic oxide may be present in an amount within the range of from 25 to about 50 wt. %.

Operating conditions within the isomerization zone are selected to maximize the production of isoalkane product from the feed components. Temperatures within the reaction zone will usually range from about 40°-235° C. (100°-455° F.). Lower reaction temperatures are generally preferred since they usually favor equilibrium mixtures of isoalkanes versus normal alkanes. Lower temperatures are particularly useful in processing feeds composed of $C_5$ and $C_6$ alkanes where the lower temperatures favor equilibrium mixtures having the highest concentration of the most branched isoalkanes. When the feed mixture is primarily $C_5$ and $C_6$ alkanes temperatures in the range of from 60° to 160° C. are preferred. Higher reaction temperatures increase catalyst activity and promote the isomerization of $C_4$ hydrocarbons. Thus, when the feed mixture contains significant portions of $C_5$-$C_6$ alkanes and the process uses a normal butane desorbent, the operating temperature should be kept below 160° C. to avoid butane isomerization. The reaction zone may be maintained over a wide range of pressures. Pressure conditions in the isomerization of $C_4$-$C_6$ paraffins range from 7 barsg to 70 barsg. Preferred pressures for this process are in the range of from 20 barsg to 30 barsg. The feed rate to the reaction zone can also vary over a wide range. These conditions include liquid hourly space velocities ranging from 0.5 to 12 hr.$^{-1}$, however, space velocities between 1 and 6 hr.$^{-1}$ are preferred. The isomerization zone will usually operate at a LHSV of about 1.5. With the additional desorbent material, it has been found that this LHSV may be increased slightly so that no net increase in the volume of the reactors in the isomerization zone is necessary to practice this invention.

Operation of the reaction zone with the preferred chlorided platinum-alumina catalyst also requires the presence of a small amount of an organic chloride promoter. The organic chloride promoter serves to maintain a high level of active chloride on the catalyst as low levels are continously stripped off the catalyst by the hydrocarbon feed. The concentration of promoter in the reaction zone is maintained at from 30 to 300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

The isomerization zone usually includes a two-reactor system with a first stage reactor and a second stage reactor in the reaction zone. The catalyst used in the process is distributed equally between the two reactors. It is not necessary that the reaction be carried out in two reactors but the use of two reactors confer several benefits on the process. The use of two reactors and specialized valving allows partial replacement of the catalyst system without taking the isomerization unit off stream. For the short periods of time during which replacement of catalyst may be necessary, the entire flow of reactants may be processed through only one reaction vessel while catalyst is replaced in the other. The use of two reaction zones also aids in maintaining lower catalyst temperatures. This is accomplished by having any exothermic reaction such as hydrogenation of unsaturates performed in a first reaction vessel with the rest of the reaction carried out in a final reaction vessel at more favorable temperature conditions.

The effluent from the reactors enters a stablilizer that removes light gases and butane from the effluent. The amount of butane taken off from the stabilizer will vary depending upon the amount of butane entering the process and the operation of the adsorption section as hereinafter described. In addition to the removal of light hydrocarbons, the stablilizer is used to reject normal and isobutane to maintain a butane balance in the total process system. The amount of normal butane rejected from the stabilizer due to the absence of an extract column is small, usually on the order of 5-15% of total normal butane in circulation. The stabilizer also removes isobutane which is major by-product from cracking side reactions that occur in the isomerization zone. The removal of additional butane from the adsorption zone will impose only minor modifications on the stabilizer. Since the amount of butane entering the system may vary from time to time, such a modification would include the addition of 5 to 10 trays and some decrease in stabilizer pressure. The stabilizer in prior art systems may normally run at 250 psia, whereas for the process of this invention, the pressure may be reduced to about 125 psia. Adjustments obvious to those skilled in the art may also be required in the stabilizer reflux to feed ratio.

When the isomerization zone is operated with a high hydrogen to hydrocarbon ratio, a separator is usually placed ahead of the stabilizer. A hydrogen-rich recycle gas stream is recovered from the separator and recycled for combination with the feed entering the isomerization zone. When the isomerization zone operates with very low hydrogen to hydrocarbon ratios the separator is not needed and the effluent from the isomerization zone may enter the stabilizer directly.

The bottoms stream from the stabilizer provides normal butanes and higher boiling hydrocarbons that include normal paraffins for recycle and isoparaffin products. The chlorides which may be present in the reaction zone will usually pose no problem for the sorbent in the adsorption zone. In normal operation, any chlorides that are present in the effluent from the isomerization zone will be removed in the overhead from the stabilizer. However, where the isomerization zone or separators downstream from the isomerization are subject to upsets, it may be desirable to provide a guard bed of some type to treat the stabilizer bottoms and prevent any carryover of chloride compounds into the adsorption section.

The effluent enters the adsorption section and is contacted with an adsorbent in an adsorption zone. This process is especially suited for adsorption systems that use multiple ports for supplying the process streams to the adsorbent and divide the adsorbent into a plurality of zones for adsorbing normal paraffins, recovering isoparaffins, purifying the adsorbent, and desorbing the normal paraffins. A well-known process of this type is the countercurrent moving bed for simulating moving bed countercurrent flow systems. Such systems have a much greater separation efficiency than fixed molecular sieve bed systems. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. The operating principles and sequence of such flow system are described in U.S. Pat. No. 2,985,589 incorporated herein by reference. In such a system it is the progressive movement of multiple liquid access points down a molecular sieve chamber that simulates the upward movement of molecular sieve contained in the chamber.

A number of specially defined terms are used in describing the simulated moving bed processes. The term "feed stream" indicates a stream in the process through which feed material passes to the molecular sieve. A feed material comprises one or more extract components and one or more raffinate components. An "extract component" is a compound or type of compound that is more selectively retained by the molecular sieve while a "raffinate component" is a compound or type of compound that is less selectively retained. In this process normal hydrocarbons from the feed stream are extract components while feed stream branched chain and cyclic hydrocarbons are raffinate components. Usually the term "extract component" as used herein refers to a more selectively retained compound or type of compound which is to be the desired product, such as normal hydrocarbons in this process. The term "displacement fluid" "or desorbent" shall mean generally a material capable of displacing an extract component. The term "displacement fluid" or "displacement fluid input stream" indicates the stream through which displacement fluid passes to the molecular sieve. The term "raffinate output stream" means a stream through which most of the raffinate components are removed from the molecular sieve. The composition of the raffinate stream can vary from about 100% displacement fluid to essentially 100% raffinate components. The term "extract stream" or "extract output stream" shall mean a stream through which an extract material which has been displaced by a displacement fluid or desorbent is removed from the molecular sieve. The composition of the extract stream can also vary from about 100% displacement fluid to essentially 100% extract components.

The term "selective pore volume" of the molecular sieve is defined as the volume of the molecular sieve which selectively retains extract components from the feed stock. The term "non-selective void volume" of the molecular sieve is the volume of the molecular sieve which does not selectively retain extract components from the feedstock. This volume includes the cavities of the molecular sieve which are capable of retaining raffinate components and the interstitial void spaces between molecular sieve particles. The selective pore volume and the non-selective void volume are generally expressed in volumetric quantities and are of importance in determining the proper flow rates of fluid required to be passed into an operational zone for efficient operations to take place for a given quantity of molecular sieve.

When molecular sieve "passes" into an operational zone (hereinafter defined and described) its non-selective void volume together with its selective pore volume carries fluid into that zone. The non-selective void volume is utilized in determining the amount of fluid which should pass into the same zone in a countercurrent direction to the molecular sieve to displace the fluid present in the non-selective void volume. If the fluid flow rate passing into a zone is smaller than the non-selective void volume rate of molecular sieve material passing into that zone, there is a net entrainment of liquid into the zone by the molecular sieve. Since this net entrainment is a fluid present in non-selective void volume of the molecular sieve, it, in most instances, comprises less selectively retained feed components.

In the preferred simulated moving bed process only four of the access lines are active at any one time: the feed input stream, displacement or disorbent fluid inlet stream, raffinate outlet stream, and extract outlet stream access lines. Coincident with this simulated upward movement of the solid molecular sieve is the movement of the liquid occupying the void volume of the packed bed of molecular sieve. So that countercurrent contact is maintained, a liquid flow down the molecular sieve chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the molecular sieve chamber into separate zones, each of which has a different function. In this embodiment of the process, it is generally necessary that three separate operational zones be present in order for the process to take place although in some instances an optional fourth zone may be used.

The retention zone, zone 1, is defined as the molecular sieve located between the feed inlet stream and the raffinate outlet stream. In this zone, the feedstock contacts the molecular sieve, an extract component is retained, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the molecular sieve between the extract outlet stream and the feed inlet stream. The basic operations taking place in zone 2 are the displacement from the non-selective void volume of the molecular sieve of any raffinate material carried into zone 2 by the shifting of molecular sieve into this zone and the displacement of any raffinate material retained within the selective pore volume of the molecular sieve. Purification is achieved by passing a portion of extract stream material leaving zone 3 into zone 2 at zone 2's upstream boundary to effect the displacement of raffinate material. The flow of material in zone 2 is in a downstream direction from the extract outlet stream to the feed inlet stream.

Immediately upstream of zone 2 with respect to the fluid flowing in zone 2 is the displacement zone or zone 3. The displacement zone is defined as the molecular sieve between the displacement fluid inlet and the extract outlet stream. The function of the displacement zone is to allow a displacement fluid which passes into this zone to displace the extract component which was retained in the molecular sieve during a previous contact with feed in zone 1 in a prior cycle of operation. The flow of fluid in zone 3 is essentially in the same direction as that of zones 1 and 2.

In some instances, an optional buffer zone, zone 4, may be utilized. This zone, defined as the molecular sieve between the raffinate outlet stream and the displacement fluid inlet stream, if used, is located immediately upstream with respect to the fluid flow to zone 3. Zone 4 would be utilized to conserve the amount of displacement fluid utilized in the displacement step since a portion of the raffinate stream which is removed from zone 1 can be passed into zone 4 to displace displacement fluid present in that zone out of the zone into the displacement zone. Zone 4 will contain enough displacement fluid so that raffinate material present in the raffinate stream passing out of zone 1 and into zone 4 can be prevented from passing into zone 3 thereby contaminating extract stream removed from zone 3. In the instances in which the fourth operational zone is not utilized, the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of molecular sieve can be accomplished by utilizing a manifold system in which the valves in the manifold are operated in a sequential manner to effect the shifting of the input and output streams thereby allowing a flow of fluid with respect to solid molecular sieve in a countercurrent manner. Another mode of operation which can effect the countercurrent flow of solid molecular sieve with respect to fluid involves the use of a rotating disc valve in which the input and output streams are connected to the valve and the lines through which feed input, extract output, displacement fluid input and raffinate output streams pass are advanced in the same direction through the molecular sieve bed. Both the manifold arrangement and disc valve are known in the art. Specifically rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of molecular sieve than some other operational zone. For instance, in some operations, the buffer zone can contain a minor amount of molecular sieve as compared to the molecular sieve required for the retention and purification zones. It can also be seen that in instances in which displacement fluid is used which can easily displace extract material from the molecular sieve that a relatively small amount of molecular sieve will be needed in a displacement zone as compared to the molecular sieve needed in the retention zone or purification zone. Since it is not required that the molecular sieve be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

In the operation of this process, at least a portion of the raffinate output stream will typically be passed to a separation means wherein at least a portion of the displacement fluid can be separated to produce a displacement fluid stream which can be reused in the process and a raffinate product containing a reduced concentration of displacement fluid. The separation means will typically be a fractionation column, the design and operation of which is well known to the separation art.

Reference can be made to D. B. Broughton U.S. Pat. No. 2,985,589, and to a paper entitled "Continuous Adsorptive Processing--A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Although both liquid and vapor phase operations can be used in may adsorptive type separation processes, liquid-phase operation is preferred for this process because of the lower temperature requirements and because of the higher yields of extract product that can be obtained with liquid-phase operation over those obtained with vapor-phase operation. Retention conditions will, therefore, include a pressure sufficient to maintain liquid phase. Displacement conditions will include the same range of temperatures and pressures as used for retention conditions.

In this invention, the extract stream does not enter any separation section for the recovery of the displacement fluid. At least a portion of the extract stream is recycled directly to the isomerization zone to provide the recycle stream as previously described. The direct recycle of the extract stream eliminates the need for a separation column and the equipment associated therewith. The elimination of the separation column for the extract stream significantly reduces the cost of the adsorption section.

Prior art processes provided a column for the separation of desorbent from the extract stream in the belief that the process could not be economically operated without such a separation. In an adsorptive separation process, the amount of adsorbed component in the feed that enters the separation zone will control the amount of selective pore volume that must be available in the adsorbent and the amount of the displacement fluid or desorbent that is needed to recover the adsorbed material from the adsorbent. Looking more specifically at the process for the separation of normal paraffins, the amount of normal paraffins in the feed mixture sets the amount of selective pore volume that must be available to process a given quantity of the feed mixture. In the case of a simulated moving bed process, an excess of adsorbent to the amount of normals in the feed mixture must be provided. In order to fully desorb all of the adsorbed components from the adsorbent, a large excess of displacement fluid or desorbent material is also needed. The circulation of the selective pore volume at a rate greater than the volumetric addition of normal paraffins and the circulation of desorbent at a rate greater than the circulation of the selective pore volume will not permit all of the desorbent material from the displacement zone to reenter the extract zone with the feed material unless there is a constantly increasing circulation of selective pore volume. Therefore, some removal of desorbent material from the extract stream is necessary in order to continuously operate the process with a constant circulation of selective pore volume.

When the feed to the adsorption zone contains normal paraffin desorbent, as well as normal paraffin extract components, the selective pore volume circulation must be increased to provide adequate pore volume for the adsorption of all normal components. However, only enough desorbent needs to be circulated in the displacement zone to displace the normal paraffin extract components and not the normal paraffin desorbent components. Accordingly, the ratio of normal paraffin desorbent to the selective pore volume circulation can be much lower than that formerly practiced in the art. This invention will use a normal paraffin desorbent flow rate to selective pore volume circulation rate below about 2. This low circulation rate reduces the amount of desorbent in the extract stream and the amount of desorbent that is recycled through the isomerization zone. Therefore, the reduced circulation rate allows the process to operate without the use of a separate desorbent recovery system or column for removing desorbent from the extract stream. A small portion of the desorbent material that passes with the extract stream through the isomerization zone is rejected in the stabilizer before it re-enters the adsorption section with the feed mixture. The amount of desorbent rejected by the stabilizer is small so that in the case of $C_5$ and $C_6$ isomerization and an adsorption section that uses a normal butane desorbent, the amount of normal butane lost through the stabilizer is small. Thus, the rejection of butane from the stabilizer has only a minor affect on the economics of the process.

When a normal butane desorbent is used, it is preferably diluted to adjust its strength. Usually the desorbent material is diluted with isobutane. The strength of the desorbent, relative to the affinity of the adsorbed components, and its flow rate into the desorption zone of the simulated countercurrent adsorption unit are related. The total desorbent flow has to increase as the n-butane concentration decreases in order to maintain recovery of the feed normal pentane and normal hexane. Such adjustments are readily accomplished, in the flow scheme of the present invention, by small adjustments in the operation of the stabilizer column.

A basic understanding of the process in the context of the isomerization of $C_4$ and $C_5$ hydrocarbons with a normal butane desorbent can be obtained from FIG. 1. Looking at FIG. 1, the $C_5$ and $C_6$ charge stock enters the process through a line 10 where it is combined an with extract stream that supplies a recycle of $C_4$-$C_6$ normal paraffins to the isomerization zone. Line 14 carries the combined feed of charge and recycle to a drier 16 after which it is combined with a recycle gas stream containing hydrogen carried by line 18. A line 20 carries the hydrogen and combined feed through a series of heat exchangers 22 and 24 that heat the feed prior to its passing through a heater 26 which raises the temperature of the mixture to the final initial reaction temperature. The fully heated hydrogen and charge mixture enter a reactor 28 that contains isomerization catalyst to perform an initial conversion of normal paraffins to isoparaffins. Effluent from reactor 28 is carried by line 30 through exchanger 24 which cools the partially converted mixture before entering a second reactor 32 where the partially converted mixture is again contacted with an isomerization catalyst at lower temperatures that favor the equilibrium conversion of isoparaffins to normal paraffins. Effluent from reactor 32 is carried by line 34 through exchanger 22 and a condensor 36 that cools the isomerization effluent for the recovery of hydrogen and other light gases in a separator 38. A recycle gas stream rich in hydrogen is taken by line 40 from separator 38, recompressed in a compressor 42, and transferred by line 18 for combination with the feed. Any additional hydrogen needed for the process is supplied by a make-up hydrogen source brought into the process by line 44. A drier 46, and a compressor 48 along the path of line 44, dry and bring the hydrogen up to process pressure before it is introduced into line 34. The hydrogen-depleted effluent from the isomerization zone is taken from separator 38 by line 50 to a stabilizer column 52. The stabilizer column removes all light gases and has a cut point that is adjusted for the removal of a desired quantity of normal butane. The overhead is transferred by a line 53 to a drum 54 from which a light gas stream is taken by line 56 and withdrawn from the process. The bottoms from the stabilizer 52 contain a mixture of normal paraffins and isoparaffins including normal butane. A line 58 transfers the stabilizer bottoms to an adsorption section.

The adsorption section uses a simulated moving bed type adsorption zone. The bottoms carried by line 58 enter adsorption section 60 as a feed mixture. Line 58 is directly connected to a rotary valve 62 which simulates the movement of adsorbent in adsorbent chamber 64 by the changing of inlet and outlet points in a manner hereinafter described. The adsorption section operates by contacting the feed mixture from line 58 with adsorbent material in adsorbent chamber 64 to provide a raffinate stream which is carried from rotary valve 62 by line 66. The raffinate stream contains isoparaffins and desorbent material which enter a raffinate column 68 that separates the desorbent material into an isoparaffin product stream taken from the bottom of raffinate column 68 via line 70 and an overhead stream of desorbent material taken from the overhead section 72 of column 68 by line 74. Line 74 transfers desorbent material to rotary valve 62 for its use in continuously displacing abstract components from adsorbent chamber 64. Extract components recovered from adsorbent chamber 64 are directed by the rotary valve into line 12 to provide the previously described recycle of $C_4$–$C_6$ normal paraffins.

Figure 2:
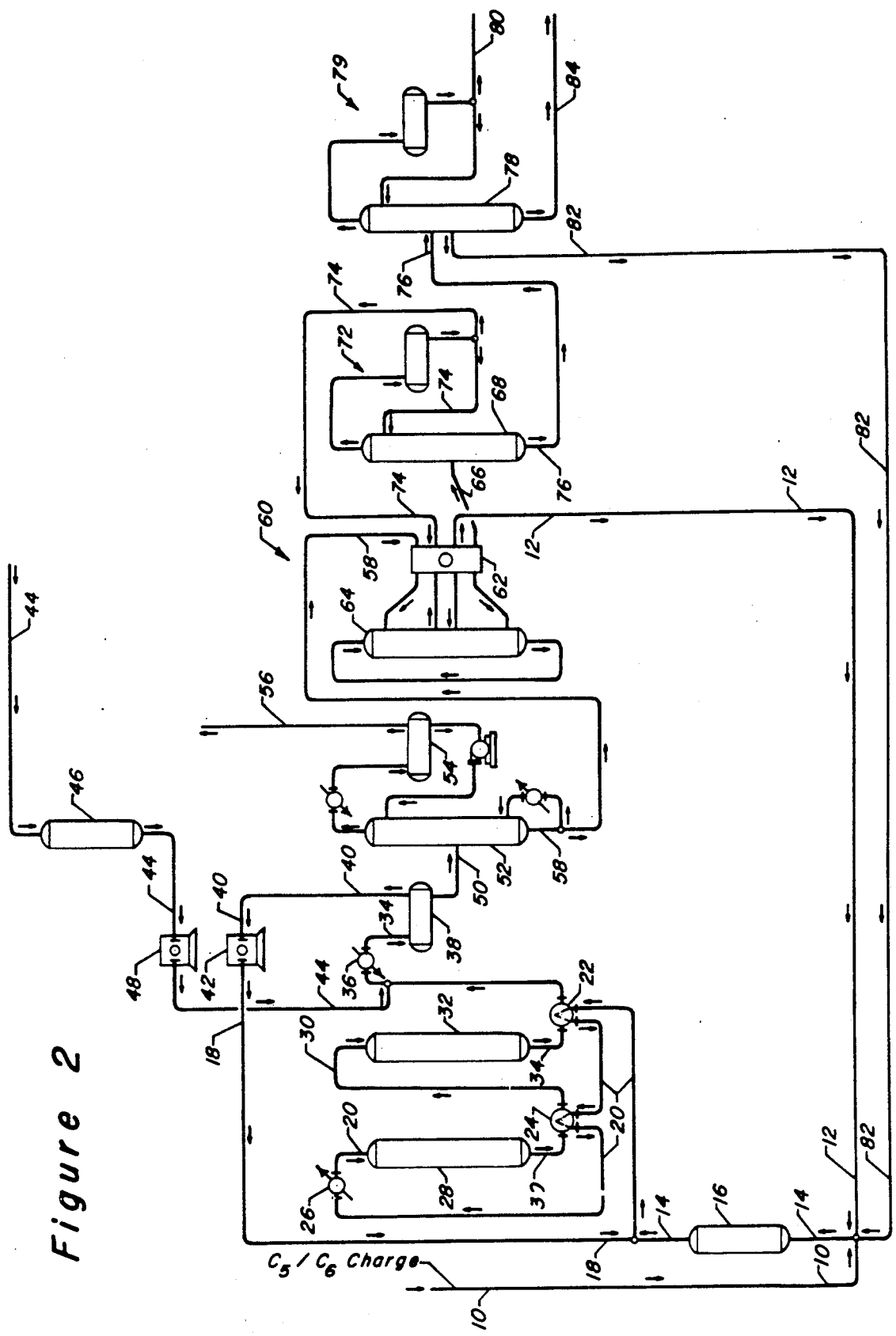
FIG. 2 shows a flow arrangement similar to that shown in FIG. 1 with the addition of a separation column for recycling isoparaffins to the isomerization zone.

In order to further improve the octane of the product stream, the raffinate column bottoms may be further separated to return relatively low octane methylpentanes to the isomerization zone for further isomerization. An arrangement for this process is shown in FIG. 2. The process shown in FIG. 2 is essentially the same as that shown in FIG. 1 except for the addition of a deisohexanizer column and an additional recycle stream to the isomerization zone. In this arrangement, the bottoms from raffinate column 68 are taken by line 76 into a deisohexanizer column 78. Column 78 is operated so that hydrocarbons having a boiling point higher than methylpentane are taken overhead and recovered as high octane product from an overhead section 79 by a line 80. Methylpentanes and higher boiling hydrocarbons can be taken from the bottom of the deisohexanizer column and recycled to the isomerization zone. FIG. 2 shows a preferred arrangement wherein methylpentanes are withdrawn as a sidecut through line 82 and recycled to the isomerization zone so that a bottoms stream comprising any $C_7$ and higher hydrocarbons may be withdrawn from the bottom of deisohexanizer column 78 through a line 84. The $C_7+$ hydrocarbon stream from the deisohexanizer can be charged to a catalytic reformer. The product stream withdrawn from line 80 will typically have a research octane number of 93 or greater.

Figure 3:
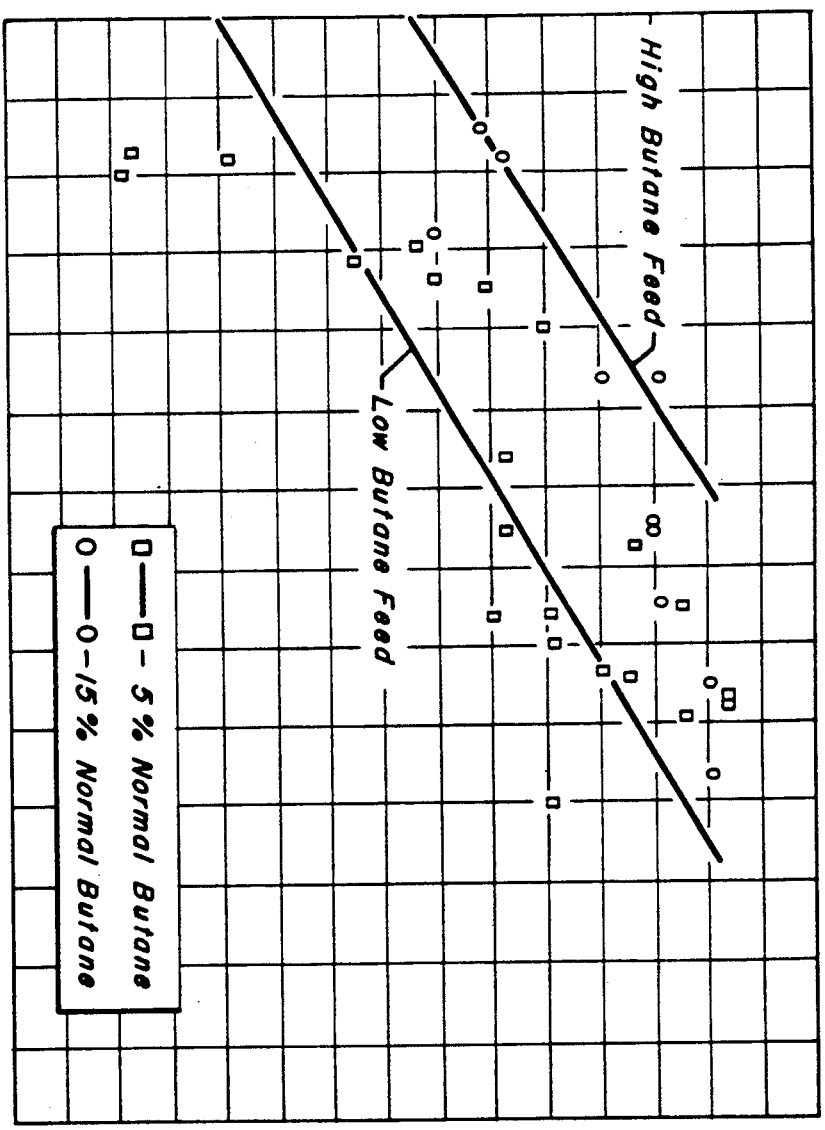
FIG. 3 is a plot of test results comparing the recovery rates for normal paraffins as a function of the volumetric flow rate of desorbent and the circulation rate of selective pore volume in the adsorption section for a high butane content feed and a low butane content feed.

The ability of the adsorption section to operate at a lower ratio of desorbent flow rate to selective pore volume circulation was verified experimentally by a series of tests. These tests were conducted in a simulated moving bed adsorption apparatus using low butane feeds and high butane feeds. The low butane and high butane feeds contained 5% and 15% normal butane. The feed was a commercially obtained isomerate whose butane concentration was adjusted (by adding n-butane) for the high butane feed tests. The simulated adsorption tests were run at temperature and pressure conditions of 200° F. and 250 psig. Conditions within the adsorption system were adjusted to obtain a normal paraffin purity in the extract stream of about 90%. The ratio of desorbent flow rate to selective pore volume circulation was varied in the test and the theoretical recovery corresponding to each ratio for each test was calculated. The experimental results of these tests are shown in FIG. 3 where points for the theoretical recovery from each test are plotted as a function of the normal paraffin desorbent rate to the selective pore volume circulation rate. The results of these experiments were approximated linearly by the line shown for high butane feed and low butane feed. Comparing the relative position of these lines at a selected recovery, it can be seen that the normal paraffin desorbent rate to selective pore volume circulation rate is approximately 30% lower for the high butane feed than for the low butane feed. This 30% reduction shows that the simulated moving bed process can be operated at a normal paraffin desorbent rate to selective pore volume circulation rate of less than two in the desorption section of the simulated moving bed process. Accordingly, it has been shown that the extract column can be eliminated from the isomerization and liquid phase adsorption process without uneconomical desorbent losses.

Therefore, it has been shown by these experiments that the normally low concentration of desorbent material in a feed stream to a liquid phase adsorption section can be increased in order to allow the direct recycle of desorbent material with the selectively retained components back to the isomerization zone. As the experimental data shows in the case of C5 and C6 isomerization, it was common practice to operate with about 5% normal butanes in the feed to the adsorption section. In this process, the concentration of desorbent material in the feed to the adsorption section is usually increased to about 10% with 15% being more typical. Although it is possible to increase the concentration of desorbent material in the feed above 15%, the additional volume circulating through the system increases the size of the reactors in the isomerization zone and other associated equipment. Since the circulation of desorbent material through the isomerization zone does not have any direct benefit to the isomerization process, the concentration of desorbent material in the feed mixture will usually not exceed 20% so that increases in equipment size and reactor volumes may be kept to a minimum.

What is claimed is:

1. A process for the isomerization of hydrocarbons, said process comprising:
    (a) passing a feed stream comprising straight chain feed hydrocarbons to an isomerization zone;
    (b) passing a recycle stream comprising straight chain feed hydrocarbons and desorbent to said isomerization zone;
    (c) contacting said feed stream and said recycle stream with an isomerization catalyst in said isomerization zone and recovering an isomerization zone effluent comprising branched chain hydrocarbons, straight chain feed hydrocarbons and desorbent;
    (d) passing said isomerization zone effluent to an adsorption section and contacting said effluent stream with an adsorbent, said adsorbent containing a desorbent in its selective pore volume and said adsorbent being selective for said straight chain feed hydrocarbons, to adsorb straight chain feed hydrocarbons and produce a first stream comprising desorbent and branched chain hydrocarbons and an adsorbent containing straight chain feed hydrocarbons in its selective pore volume;
    (e) separating desorbent from said first stream and recovering a product stream rich in branched chain hydrocarbons; and
    (f) desorbing said straight chain feed hydrocarbons from said adsorbent containing straight chain feed hydrocarbons by passing a volume of desorbent to said adsorbent containing straight chain feed hydrocarbons that is less than twice the selective pore volume of the absorbent containing straight chain feed hydrocarbons and contacting said adsorbent with said quantity of desorbent to produce said recycle stream comprising straight chain hydrocarbons and desorbent and said adsorbent-containing desorbent.

2. The process of claim 1 wherein said straight chain feed hydrocarbons comprise $C_5$ and $C_6$ hydrocarbons and said desorbent comprises normal butane.

3. The process of claim 1 wherein said isomerization catalyst comprises alumina having from 0.01 to 25 wt. % platinum and from 2 to 10 wt. % of a chloride component.

4. The process of claim 2 wherein said isomerization effluent is passed through a stabilizer section to remove light hydrocarbons and the isomerization effluent recovered from said stabilizer section has a normal butane content equal to 10 to 20 wt. % of the normal paraffins in said effluent.

5. The process of claim 1 wherein said adsorption section comprises at least one bed of adsorbent, the total quantity of adsorbent is divided into at least three operationally distinct zones of adsorbent, said effluent and desorbent are charged to different zones and the position of the zones relative to said total quantity of said adsorbent is at least intermittently varied by changing withdrawal and input points for said feed and desorbent.

6. The process of claim 2 wherein said product stream comprises $C_5$ and $C_6$ isoparaffins, said product stream enters a deisohexanizer zone, a high octane stream comprising isopentane and lower boiling hydrocarbons is recovered from said deisohexanizer and a second recycle stream comprising methylpentane is recycled to said isomerization zone.

7. A process for the isomerization of hydrocarbons said process comprising:
 (a) passing a feed stream comprising normal paraffins to an isomerization zone;
 (b) passing a recycle stream comprising normal paraffins and a desorbent material to said isomerization zone;
 (c) contacting said feed stream and said recycle stream with an isomerization catalyst in said isomerization zone and recovering an isomerization zone effluent comprising isoparaffins, normal paraffins and desorbent material;
 (d) passing at least a portion of said isomerization zone effluent to an adsorption section as a feed mixture and therein contacting said feed mixture with an adsorbent selective for normal paraffins and separating said isoparaffins from said normal paraffins by:
  (i) maintaining a net fluid flow through at least three operationally distinct and serially interconnected zones of adsorbent in said adsorption section;
  (ii) maintaining an adsorption zone in said section, said adsorption zone being defined by the adsorbent located between a feed input stream at an upstream boundary of said zone, and a raffinate output stream at a downstream boundary of said zone;
  (iii) maintaining a purification zone immediately upstream from said adsorption zone, said purification zone being defined by the adsorbent located between an extract output stream at an upstream boundary of said purification zone and said feed input stream at a downstream boundary of said purification zone;
  (iv) maintaining a desorption zone immediately upstream from said purification zone, said desorption zone being defined by the adsorbent located between a desorbent input stream at an upstream boundary of said zone and said extract output stream at a downstream boundary of said zone;
  (v) passing said feed mixture into said adsorption zone at adsorption conditions to effect the selective adsorption of said normal paraffins by said adsorbent in said adsorption zone and withdrawing a raffinate output stream from said adsorption zone;
  (vi) passing said desorbent material into said desorption zone at desorption conditions to effect the displacement of said normal paraffins from the adsorbent in said desorption zone;
  (vii) withdrawing an extract output stream comprising said normal paraffins and desorbent material from said desorption zone;
  (viii) withdrawing a raffinate output stream comprising said isoparaffins and desorbent material from said adsorption zone; and
  (ix) periodically advancing through said column of adsorbent in a downstream direction with respect to fluid flow in said adsorption zone, the feed input stream, raffinate output stream, desorbent input stream and extract output stream to effect the shifting of zones through said adsorbent and the production of extract output and raffinate output streams;
 (e) separating desorbent material from said raffinate output stream and returning at least a portion of said desorbent material to said adsorption zone as said desorbent input stream and recovering a product stream rich in isoparaffins; and
 (f) returning at least a portion of said extract output stream directly to said isomerization zone without intermediate separation as said recycle stream.

8. The process of claim 7 wherein said feed stream comprises $C_5$ and $C_6$ hydrocarbons and said desorbent comprises normal butane.

9. The process of claim 8 wherein said isomerization catalyst comprises alumina having from 0.01 to 25 wt. % platinum and from 2 to 10 wt. % of a chloride component.

10. The process of claim 9 wherein said isomerization effluent is passed through a stabilizer section and a stabilized stream containing a normal butane concentration equal to 10–20 wt. % of the normal paraffins and said isomerization effluent is passed to said adsorption section as said feed mixture.

11. The process of claim 10 wherein said product stream comprises $C_5$ and $C_6$ isoparaffins, said product stream enters a deisohexanizer zone, the product stream is separated into at least a high octane stream comprising isopentane and lower boiling hydrocarbons, and a second recycle stream comprising methylpentanes, the high octane stream is recovered from said deisohexanizer, and the second recycle stream is recycled to said isomerization zone.

12. The process of claim 11 wherein said deisohexanizer zone comprises a deisohexanizer column, said second recycle stream is withdrawn from said deisohexanizer column as a sidecut stream and hydrocarbons having boiling points higher than methylpentane are withdrawn from the bottom of said deisohexanizer column.

13. The process of claim 10 wherein said stabilizer rejects butanes to maintain the normal butane concentration in said feed mixture.

14. The process of claim 7 wherein the quantity of desorbent material passing through said desorption zone is less than twice the selective pore volume of adsorbent material in said desorption zone.

15. A process for the isomerization of $C_5$ and $C_6$ hydrocarbons said process comprising:

(a) passing a feed stream comprising $C_5$ and $C_6$ normal paraffins to an isomerization zone;

(b) passing a recycle stream comprising $C_5$ and $C_6$ normal paraffins in admixture with a normal butane desorbent to said isomerization zone;

(c) contacting said feed stream and said recycle stream with an isomerization catalyst in said isomerization zone and recovering an isomerization zone effluent comprising $C_5$ and $C_6$ isoparaffins, $C_5$ and $C_6$ normal paraffins and said butane desorbent;

(d) passing said isomerization zone effluent to a stabilizer section and separating said effluent into an overhead stream containing butane and any lighter materials and a stabilized stream comprising $C_5$ and $C_6$ normal paraffins, $C_5$ and $C_6$ isoparaffins and normal butane in an amount equal to 10-20 wt. % of $C_5$ and $C_6$ normal paraffins in said stabilized stream;

(e) passing at least a portion of said stabilized stream to an adsorption section as a feed mixture and therein contacting said feed mixture with an adsorbent selective for normal paraffins and separating said isoparaffins from said normal paraffins by:

(i) maintaining a net fluid flow through at least three operationally distinct and serially interconnected zones of adsorbent in said adsorption section;

(ii) maintaining an adsorption zone in said section, said adsorption zone being defined by the adsorbent located between a feed input stream at an upstream boundary of said zone and a raffinate output stream at a downstream boundary of said zone;

(iii) maintaining a purification zone immediately upstream from said adsorption zone, said purification zone being defined by the adsorbent located between an extract output stream at an upstream boundary of said purification zone and said feed input stream at a downstream boundary of said purification zone;

(iv) maintaining a desorption zone immediately upstream from said purification zone, said desorption zone being defined by the adsorbent located between a desorbent input stream at an upstream boundary of said zone and said extract output stream at a downstream boundary of said zone;

(v) passing said feed mixture into said adsorption zone at adsorption conditions to effect the selective adsorption of said normal paraffins by said adsorbent in said adsorption zone and withdrawing a raffinate output stream from said adsorption zone;

(vi) passing a normal butane desorbent into said desorption zone in a quantity that is less than twice the selective pore volume of adsorbent in desorption zone at desorption conditions to effect the displacement of $C_5$ and $C_6$ normal paraffins from the adsorbent in said desorption zone;

(vii) withdrawing an extract output stream comprising $C_5$ and $C_6$ normal paraffins and a normal butane desorbent from said desorption zone;

(viii) withdrawing a raffinate output stream comprising $C_5$ and $C_6$ isoparaffins and normal butane desorbent from said adsorption zone; and (ix) periodically advancing through said column of adsorbent in a downstream direction with respect to fluid flow in said adsorption zone, the feed input stream, raffinate output stream, desorbent input stream and extract output stream to effect the shifting of zones through said adsorbent and the production of extract output and raffinate output streams;

(f) separating normal butane from said raffinate output stream and returning at least a portion of said normal butane to said adsorption zone as said desorbent input stream and recovering a product stream rich in $C_5$ and $C_6$ isoparaffins; and (g) returning at least a portion of said extract output stream directly to said isomerization zone without intermediate separation as said recycle stream.

16. The process of claim 15 wherein said product stream enters a deisohexanizer column, a high octane stream comprising isopentane and lower boiling hydrocarbons is recovered from said deisohexanizer column and a second recycle stream comprising methylpentane is withdrawn from said column.

17. The process of claim 15 wherein a bottoms stream comprising hydrocarbons having boiling points higher than methylpentane is withdrawn from said column.

* * * * *